United States Patent [19]

Hall et al.

[11] Patent Number: 5,105,815
[45] Date of Patent: Apr. 21, 1992

[54] NON-INVASIVE MONITORING OF CARDIAC OUTPUT

[75] Inventors: Peter R. Hall, Dyfed; Jack Trehearne, London; Dawood Parker; Paul Clancy, both of Dyfed, all of United Kingdom

[73] Assignee: Abbey Biosystems Limited, Swansea, Wales

[21] Appl. No.: 556,311

[22] Filed: Jul. 20, 1990

Related U.S. Application Data

[62] Division of Ser. No. 253,007, Oct. 4, 1988, Pat. No. 5,022,410.

[51] Int. Cl.⁵ .............................................. A61B 8/06
[52] U.S. Cl. .............................................. 128/661.08
[58] Field of Search ..................... 128/661.08–661.10, 128/696, 713

[56] References Cited

U.S. PATENT DOCUMENTS 4,137,910  2/1979  Murphy ........................... 128/713 X
4,501,279  2/1985  Seo ................................. 128/661.1

OTHER PUBLICATIONS

Wells; M. K. et al., "UTS Transesophogeal Measurement of Cardiac Output", Conf. 1978 Advances in Bioengr., San Francisco, Calif., U.S.A. (Dec. 10–15, 1978).

Primary Examiner—Francis Jaworski
Attorney, Agent, or Firm—Howard F. Mandelbaum

[57] ABSTRACT

A device for positioning/retaining a transducer relative to a body characterized in that it comprises a supporting member for placement on the body, connected thereto one end of a flexible and elongate arm, which has a mount for the transducer at or near the remote end thereof, and means for locking the arm in a fixed position relative to the body is disclosed.

Also disclosed are an apparatus for monitoring aortic blood velocity and derived parameters by Doppler ultrasound and, optionally, ECG comprising such a device and that use of such an apparatus.

2 Claims, 4 Drawing Sheets

NON-INVASIVE MONITORING OF CARDIAC OUTPUT

This application is a divisional of U.S. patent application Ser. No. 07/253,007 filed Oct. 4, 1988 and now U.S. Pat. No. 5,022,410 to Hall et al. for Non-Invasive Monitoring of Cardiac Output.

BACKGROUND AND SUMMARY OF THE INVENTION

This invention relates to a non-invasive cardiac output monitor; more particularly, it relates to a device for long-term or continuous use in such monitoring.

The continuous monitoring of aortic blood velocity and derived parameters by Doppler ultrasound or monitoring by a combination of ECG and Doppler ultrasound have not previously been done.

In simple terms, non-invasive monitoring of cardiac output means determination of the quantity of blood pumped by the heart, without entering the body. The use of ultrasound equipment has been proposed for this purpose, but such is attended by significant problems. Unless the user has a high level of skill, the results are unreliable since there is no means for the equipment to distinguish between systolic, i.e. wanted, blood flow and diastolic, i.e. unwanted blood flow. Additionally, there is no means for the system to assess signal-to-noise ratio of the flow signals, a function which is necessary since poor signal-to-noise ratio causes erroneous measurements. Furthermore, for meaningful measurement, the transducer must be accurately positioned and must be held in place in such a way that appropriate pressure is applied. Attempts to position the transducer using, for example, adhesive tape are, at best, only partially successful. Moreover, particularly for longterm use, the positioning means must not cause unnecessary discomfort to the patient and must allow body movement without disturbing the monitoring.

The present invention satisfies requirements for distinguishing between systolic and diastolic flow, assessing signal-to-noise ratio and transducer positioning for long term use, and offers significant advantages to a clinician.

In general terms, a cardiac output monitor based on the ultrasound technique will typically comprise the following units; a transducer, containing the ultrasound transmitter/receiver elements, which is manually held in place in the patient's suprasternal notch. The transducer is connected to the main instrument by a cable. The instrument contains a Doppler front end system which generates and receives the ultrasound signals, to and from the transducer, respectively, and which provides an audio output of the Doppler-shifted ultrasound. This audio signal is then passed to a spectrum analyzer or zero crossing counter which extracts, in real time, the maximum frequency present containing significant energy. The maximum frequency present during systole represents aortic blood velocity, hence an integration of this function, for each beat, represents the distance travelled by the blood during each beat. This is commonly referred to as "stroke distance". Aortic cross-sectional area is then determined, either by direct measurement, or by the use of a nomogram. Stroke distance multiplied by aortic cross-sectional area, multiplied by pulse rate then equals cardiac output, a calculation typically performed in software. The thus-obtained cardiac output value may then be displayed on LED's or LCD's. In use, the transducer is manually positioned in the suprasternal notch and manipulated until some predetermined criterion is maximised, for example the pitch of sound heard via the loudspeaker, the cardiac output value displayed or the peak frequency as displayed on a bar-graph. The thus-obtained cardiac output value is noted and the transducer is removed. In general, such instruments have not been well accepted by medical staff. One of the main problems is that they tend to be unreliable, that is, the instruments are susceptible to the interfering effects of other flows and movements of patient organs relative to the transducer. Erroneous results may occur, without the user being aware. Another major problem is that, as in the invasive techniques that the ultrasound methods seeks to replace, measurements are intermittent only. A continuous method of monitoring cardiac output is far more desirable since it enables monitoring throughout therapeutic manoeuvres and exercise tests, for example.

Surprisingly, it has now been possible to design an advantageous ultrasound sensor and instrument which overcomes these problems to a significant degree.

The present invention provides a device for positioning/retaining a transducer relative to a body characterised in that it comprises a supporting member for placement on the body, connected thereto one end of a flexible and elongate arm, which has a mount for the transducer at or near the remote end thereof, and means for locking the arm in a fixed position relative to the body.

Generally, the arm comprises a plurality of interengaging segments threaded on a wire. The tensioning wire may be of solid construction, but, if woven as is preferable, the cable is such that axial twisting on changing tension is minimised. The segments may be locked in position by a tensioning means, which may be of the screw and lever—type or the cam and lever—type. The same or different material may be used for the segments, which either all have one generally convex face and an opposing generally concave face or alternate between those having both faces generally concave and those having both faces generally convex.

The present invention also provides an apparatus for monitoring aortic blood velocity and derived parameters by Doppler ultrasound and/optionally, ECG comprising the present device and further provides that use of such an apparatus.

According to the present invention, there is provided a sensor device which is particularly suitable for use in non-invasive monitoring of cardiac output. In general terms, the present device is a positioning/retaining means for a transducer, for example a conventional ultrasound transducer, on the body surface, in particular making firm contact in the suprasternal notch. In accordance with the present invention, a transducer is mounted at one end of a flexible/fixable arm, a so-called 'lockable snake', and may be conventionally connected to the Doppler front end inside the instrument. The "lockable snake" comprises threaded segments each possessing a concave face and a convex face in a preferred embodiment, mating with adjacent segments. The segments are commonly made of glass loaded polycarbonate. Generally, such segments are threaded on a suitable wire. At the end of the 'lockable snake' remote from the transducer is a tensioning means. Until tension is applied to the wire, the segments may move relative to one another, resulting in a flexible 'snake', which allows positioning as desired. Once the transducer is located as required, tension may be applied to the wire, thus 'engaging' the segments and holding the configuration. Tension may be applied by various known means, commonly relying on screw and lever and cam adjustment. The tensioning means end of the snake is mounted on a supporting member. For example, a three-legged plastic supporting member may be used, which may be fixed to a patient's chest so that the transducer may be positioned as required. The supporting member may be fixed to the chest in various ways. It may be stuck in place with adhesive pads or held in place by an elasticated strap or straps or by a combination of such means, for example. A particularly convenient combination is to use standard ECG electrodes as a method of adhesion, together with a single neck strap. This provides the ECG signals needed by the main instrument from the same sensor as provides the Doppler signals. Otherwise, the ECG signal may be obtained by a standard, separate ECG lead.

BRIEF DESCRIPTION OF THE DRAWINGS

For purposes of exemplification, two embodiments of the present invention will now be further described with reference to the accompanying illustrative drawings.

DETAILED DESCRIPTION OF THE PREFERRED EMBODIMENTS

Figure 1:
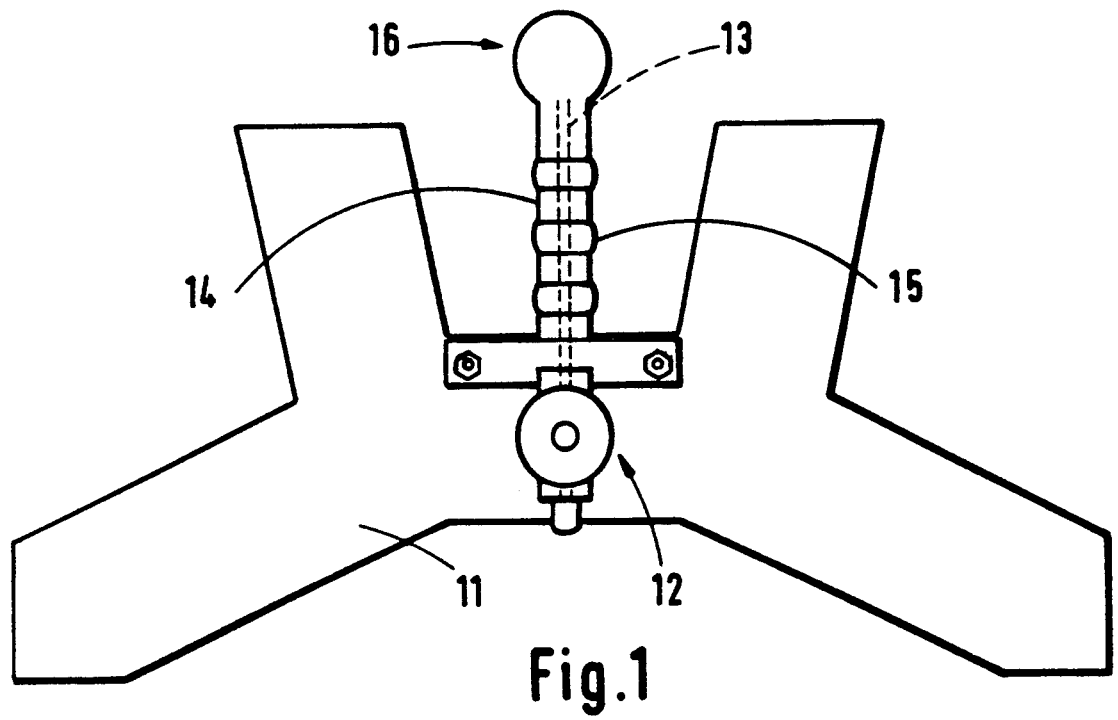
FIG. 1 shows an illustrative plan view of a device in accordance with the present invention.

Referring to accompanying illustrative FIG. 1, in one embodiment a supporting member 11 carries a tensioning means 12. The tensioning means controls the tension in a wire 13 on which are threaded alternating generally cylindrical and generally spherical segments 14 and 15, respectively, which together constitute a "lockable snake". Mounted on the remote end of the snake is a transducer 16, which is connected to suitable monitoring equipment (not shown).

Figure 2:
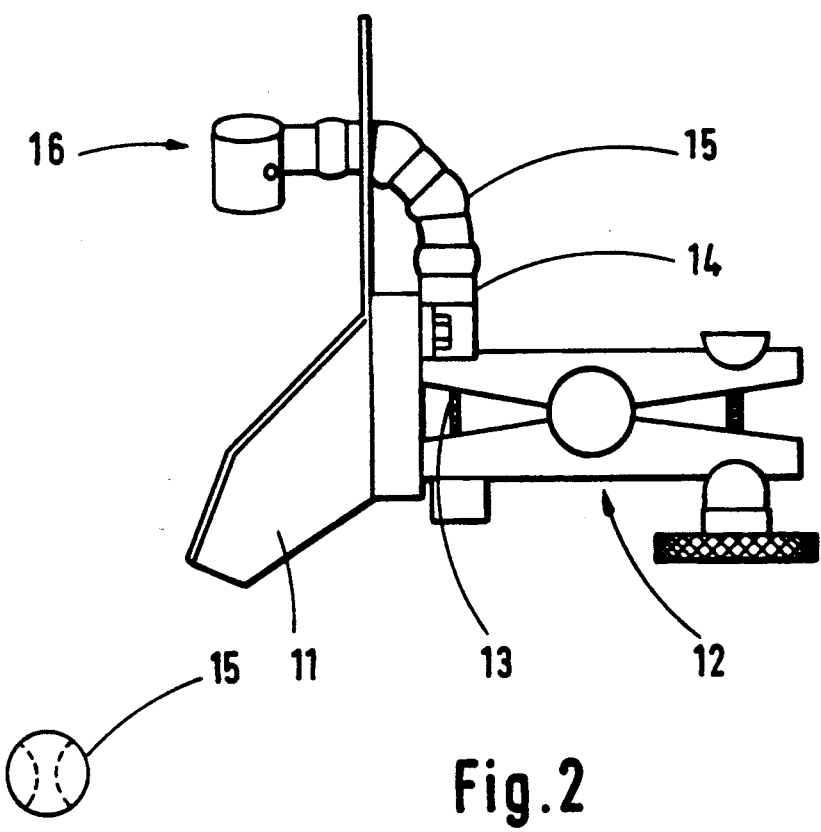
FIG. 2 shows an illustrative side view thereof.

Corresponding reference numerals are used in accompanying illustrative FIG. 2. As may be seen from this embodiment, the supporting member 11 may be contoured as desired to fit a patient's body and may hold the mounting of the "snake" clear thereof. Also shown, in section, is a spherical segment 15.

Figure 3:
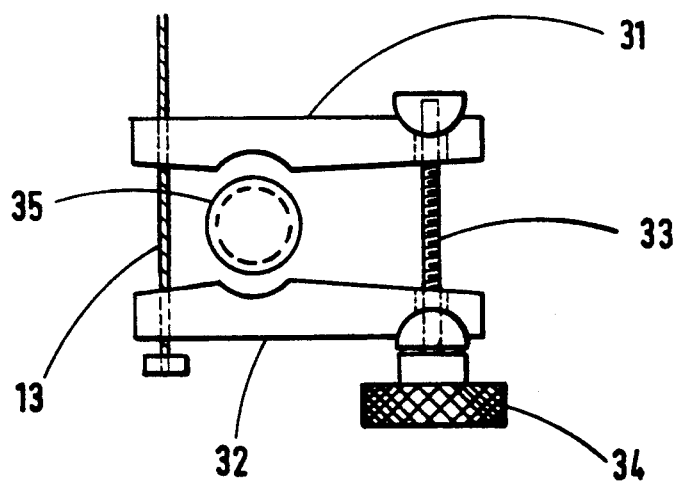
FIG. 3 shows an illustrative detail of a tensioning means.

Accompanying illustrative FIG. 3 details a tensioning means as depicted in FIGS. 1 and 2, respectively. Basically, pivoted members 31, 32 (pivoted at 35) are provided such that the wire 13 passes through the member 31 nearest the "snake" bearing the transducer and is attached to or fixed at the other 32. By opening or closing the pivoted member, tension is applied or released. A screw thread arrangement, 33 is conveniently used which is adjusted by means of knob 34.

In such a case, the device may be fixed to the chest using two elasticated straps, one round each arm, the ends of which are attached to the extremities of the supporting member. ECG signals may be obtained by a standard set of ECG leads and electrodes.

Figure 4:
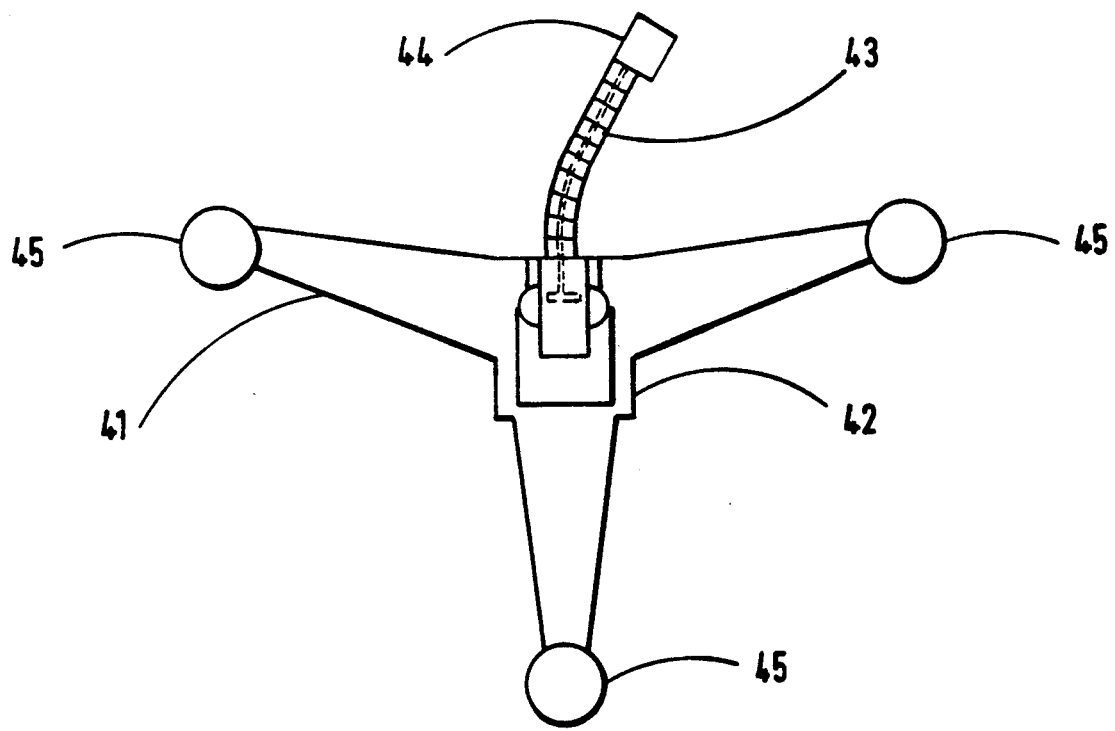
FIGS. 4, 5 and 6 show similar illustrations of a preferred embodiment.
Figure 5:
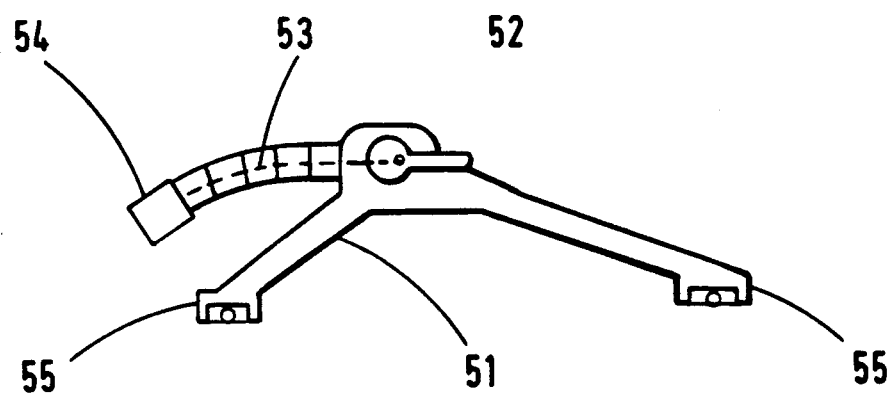

Referring to accompanying illustrative FIGS. 4 and 5, in a preferred embodiment a supporting member 41 or 51 carries a tensioning means 42 or 52. The tensioning means controls the tension in a wire 43 or 53, on which are threaded segments, each having a part-spherical concave face, which together constitute a "lockable snake". Mounted on the remote end of the snake is a tranducer 44 or 54 which is connected to suitable monitoring equipment (not shown).

Additionally, at the tip of each of the three 'legs' of the supporting member in this embodiment is a press-stud socket 45 or 55 of such a size as to accept a standard ECG electrode press stud. The ECG electrodes may thus be connected to or disconnected from the supporting member. Electrical connections are made internally to the press-stud sockets to obtain the ECG signals themselves.

Figure 6:
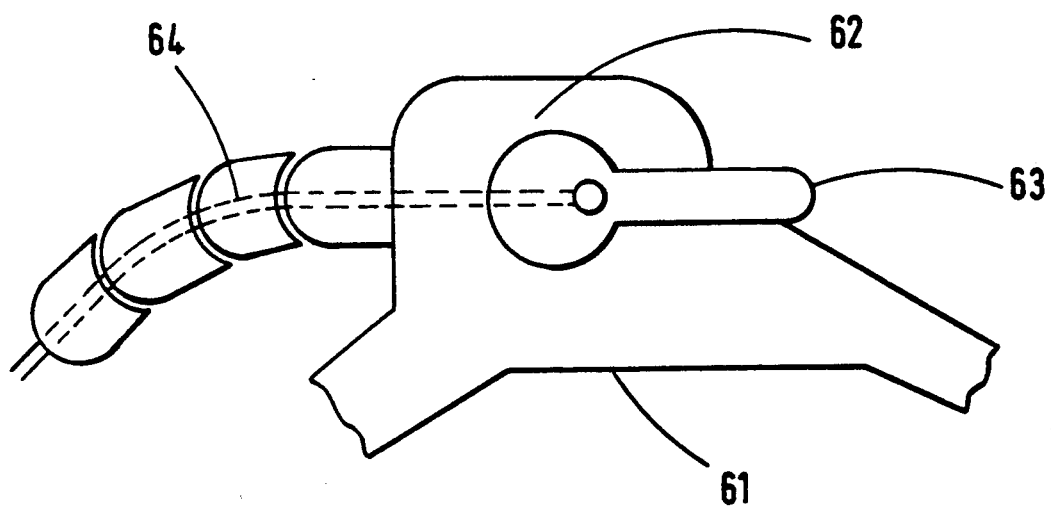

Accompanying illustrative FIG. 6 details the tensioning means as depicted in FIGS. 4 and 5. Basically, a fixed member 61 is provided which contains a rotating member 62, turned by means of a lever 63. The rotating member is drilled longitudinally, off-centre, and the thus-formed hole contains a ferrule into which the end of the wire 64 is fixed. The rotating member thus forms a cam, which applies tension when it is lowered.

Surprisingly, it has been discovered that by the use of a combination of Doppler ultrasound and ECG techniques, a more reliable measurement of systolic aortic blood velocity and hence cardiac output, is possible. In accordance with the present invention, there may be a software algorithm implemented using data from Doppler ultrasound and ECG which is particularly suitable for non-invasive monitoring of cardiac output.

The QRS complex of the ECG signal may be used as a timing reference to discriminate between systole and diastole. For example, systole may be defined as the first half of the interbeat period and diastole the second half. The desired aortic blood flow signal from the Doppler sensor occurs almost exclusively during systole. However, during diastole, signals emanating from the Doppler sensor are almost exclusively unwanted, for example flows or movements other than aortic blood flow, or electrical noise. For each heart-beat, the character of the Doppler signal whether amplitude or frequency content or both may be analysed for systole and diastole separately, by use of the ECG timing reference. Firstly, only Doppler signals obtained during systole may be used in the cardiac output computation. Secondly, the ratio of a parameter of the Doppler signal may be taken between systole and diastole, as a measure of signal quality and hence reliability. For example, maximum frequency of significant energy may be integrated over systole and compared with that integrated over an equal time in diastole. If the ratio of these values systole: diastole fails to reach a certain threshold, the beat is discarded as invalid or noisy. Otherwise, it is accepted as valid.

This ability of the instrument to discriminate between noisy and clear beats contributes greatly to its reliability.

A further advantage of the systole/diastole discrimination is that automatic gain control systems in the Doppler signal path may be configured to be activated only during systole. This improves the efficiency and speed of response thereof.

Figure 7:
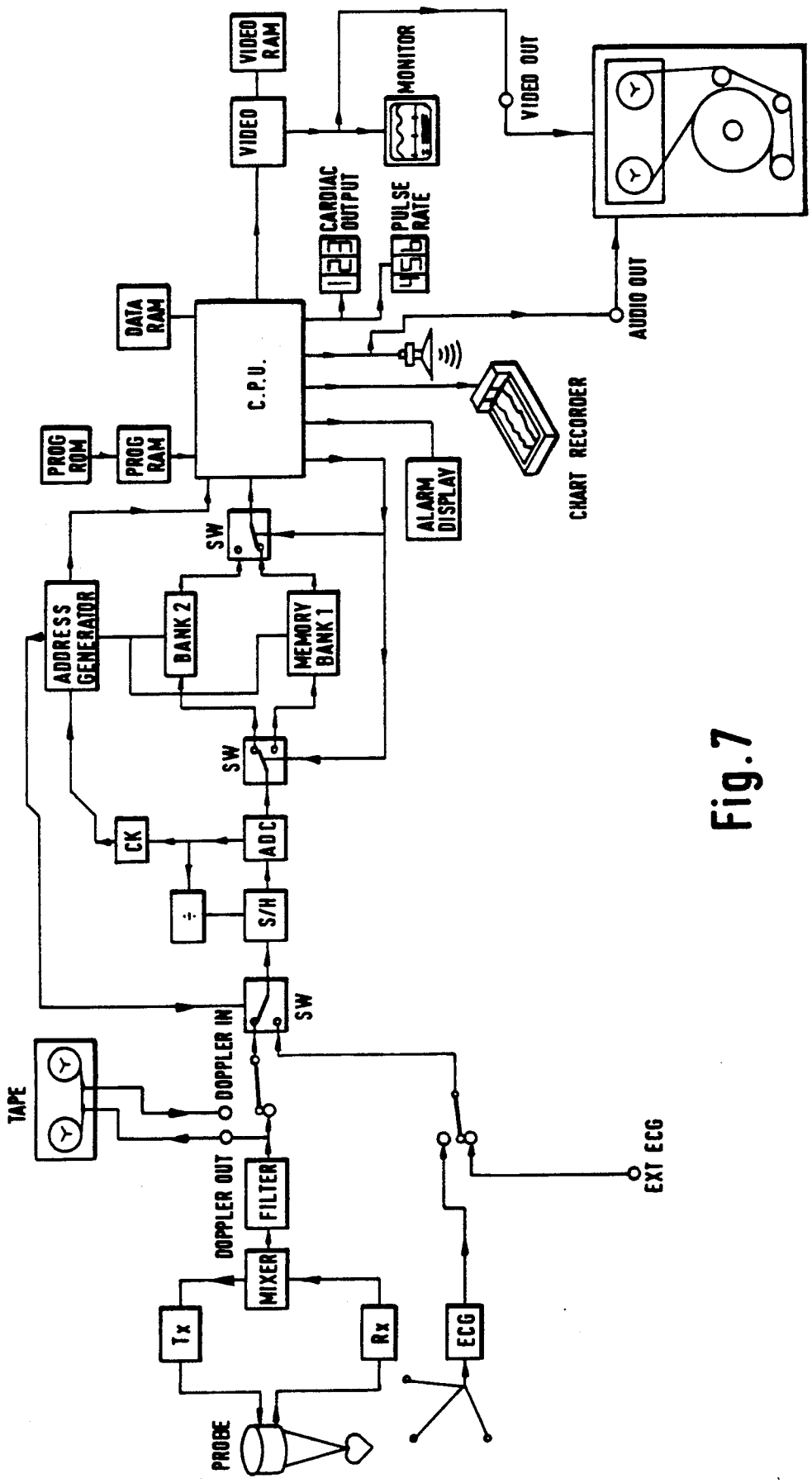
FIG. 7 shows an illustrative block diagram of an instrument embodying the present invention.

For purposes of further exemplification, a prototype version of an instrument incorporating the present invention will now be described. Accompanying illustrative FIG. 7 is a block diagram of such an instrument. At the left-hand side of the diagram, the probe or transducer is connected to a conventional ECG front end. There are facilities for recording and replaying these signals. Sampling Doppler signals at 25 KHz and ECG signals at 100 Hz, the data are taken via a double buffered memory system into the central processor unit or CPU. Here, spectral analysis is performed and all algorithms and calculations necessary for cardiac output computation are carried out. Numerical results are sent to seven segment LEDs for display, while graphical displays of the Doppler and ECG signals are sent to a CRT unit. A video output is provided.

In use, (with reference to the preferred sensor illustrated) a standard ECG electrode is 'popped' into the connector on each of the feet of the sensor. The sensor plus electrodes is then stuck onto the chest, such that the ultrasound transducer is within reach of the suprasternal notch. A neck strap is then positioned behind the patient's neck, with each end connecting to one of the two upper legs of the sensor.

The main instrument is switched on, and the sensor connected. Patient details are entered, via the keyboard, so that the instrument may estimate aortic cross-sectional area. Monitoring then commences and an ECG trace appears on the screen. Thereafter, the Doppler ultrasound sensor needs to be positioned.

The transducer is unlocked by raising the locking level, ultrasound gel is applied to the transducer face and the transducer is positioned in the suprasternal notch. The transducer is then scanned vertically and horizontally until the optimum systolic blood flow signals are received. The criteria for this are highest peak systolic velocity and acceleration, and minimum diastolic noise displayed on the CRT. When the transducer is optimally positioned, the locking lever is pressed down, to lock the transducer in position, and allow hand-off monitoring to begin.

We claim:

1. A method of monitoring the cardiac output of a patient comprising
   monitoring ECG signals from the patient to determine systole and diastole portions of the period between heart beats,
   monitoring Doppler signals from the patient to determine rate of blood flow including measuring a parameter of the Doppler signal during systole, measuring said parameter of the Doppler signal during diastole, computing the ratio between said parameter of the Doppler signal during systole and said parameter of the Doppler signal during diastole, and rejecting the Doppler signal if said ratio is beyond a predetermined threshold value, and
   computing the blood flow volume from the Doppler signals obtained substantially only during the systole portion of the period between heart beats.

2. A method of monitoring the cardiac output of a patient according to claim 1 wherein said parameter is maximum frequency of significant energy integrated over time.

* * * * *